United States Patent [19]

Alena et al.

[11] Patent Number: 4,803,991

[45] Date of Patent: Feb. 14, 1989

[54] THREE ELECTRODE HYDROQUINONE SUBCUTANEOUS EQUILIBRATING TONOMETER

[75] Inventors: Richard L. Alena; William H. McIntyre, both of San Francisco, Calif.

[73] Assignee: Baxter Healthcare Corporation, Irvine, Calif.

[21] Appl. No.: 911,277

[22] Filed: Sep. 24, 1986

[51] Int. Cl.⁴ ................................................ A61B 5/00
[52] U.S. Cl. .................................... 128/635; 204/403; 204/412; 204/415; 204/431
[58] Field of Search ............... 128/635; 204/403, 406, 204/412, 415, 431

[56] References Cited

U.S. PATENT DOCUMENTS

| | | | |
|---|---|---|---|
| 2,913,386 | 11/1959 | Clark, Jr. | 204/415 |
| 3,380,905 | 4/1968 | Clark, Jr. | 204/415 |
| 3,905,888 | 9/1975 | Mindt et al. | 128/635 X |
| 3,919,067 | 11/1975 | Carson, Jr. et al. | 204/412 |
| 3,957,613 | 5/1976 | Macur | 128/635 X |
| 4,400,242 | 8/1983 | Albery | 204/415 X |
| 4,512,349 | 4/1985 | Hunt et al. | 128/632 |

Primary Examiner—Lee S. Cohen
Attorney, Agent, or Firm—Townsend and Townsend

[57] ABSTRACT

A closed tonometer for subcutaneous insertion is disclosed having a small closed equilibrating bath. Three noble metal electrodes, preferably platinum (Pt), communicate through electrical conductors to the bath at spacings exceeding 0.2 mm. Each noble metal electrode is typically exposed to the bath by embedding the noble metal in a dielectric and cutting both dielectric and electrode so that the exposed electrode is flush with and a part of the closed bath wall. The bath is contained within an oxygen permeable membrane -- preferably Silastic ® a registered trademark of Dow Corning Corporation of Midland, Michigan. The bath contains a sodium chloride (NaCl) solution, preferably 0.9%, and small amounts of a hydroquinone such as a tenth of a gram of pure ascorbic acid per 30 ml of NaCl solution. One of the noble metal electrodes becomes a quinhydrone reference electrode preserving a precise voltage differential with respect to the electrolyte bath. This voltage of the quinhydrone reference electrode is passed through a voltage follower amplifier to a voltage adder where it is added to a reference bias voltage. Output from the adder passes to a second electrode serving as an anode. The anode supplies current to the enclosed bath sufficient to maintain the bath at constant voltage with respect to the cathode. The current at the cathode is thus solely a function of oxygen tension equilibrated from the measured tissue. There results a tonometer of miniature dimension having true analytical output.

8 Claims, 2 Drawing Sheets

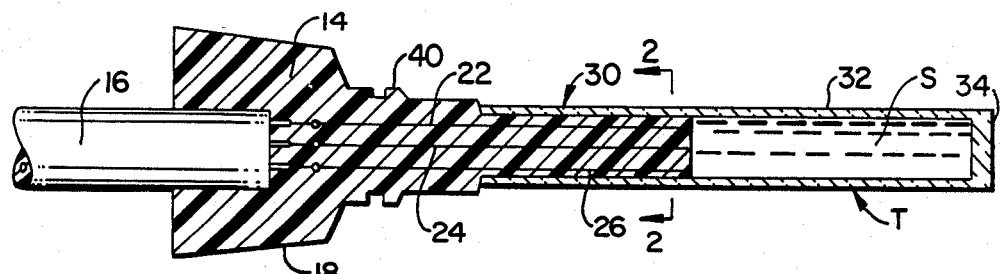
FIG._1.
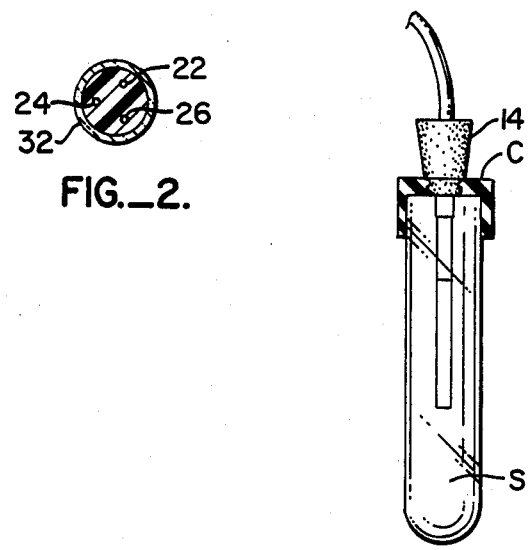
FIG._2.
FIG._3.
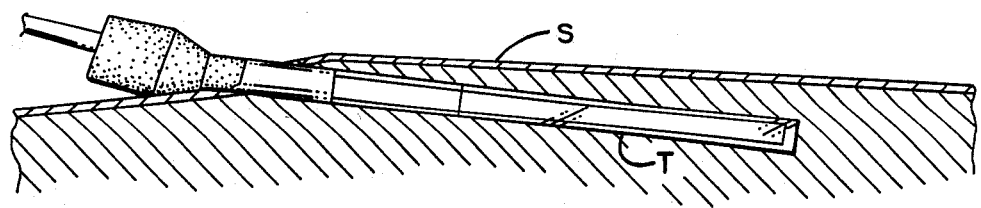
FIG._4.

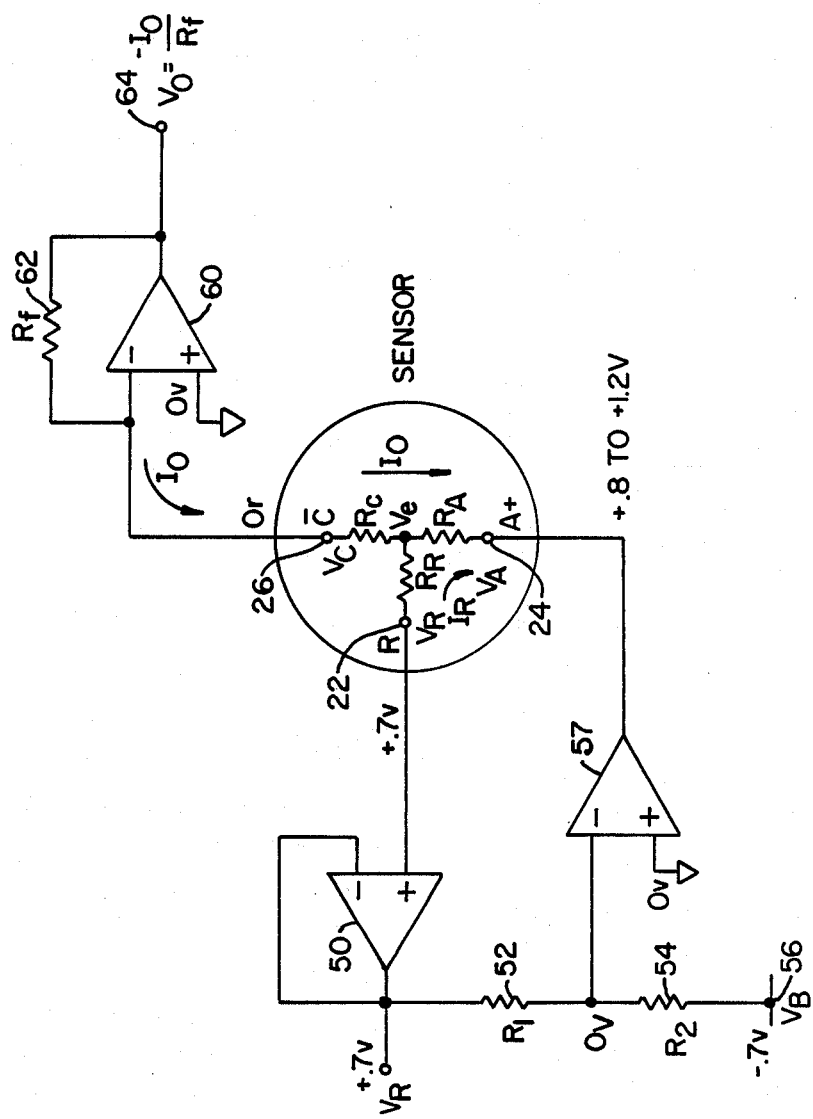
FIG._5.

THREE ELECTRODE HYDROQUINONE SUBCUTANEOUS EQUILIBRATING TONOMETER

This invention relates to subcutaneous tonometers and more particularly to a three electrode tonometer utilizing a hydroquinone solution.

SUMMARY OF THE PRIOR ART

Oxygen sensors using polarographic techniques to measure oxygen tension across semi-permeable membranes are known. Typically, such oxygen sensors are provided with a silver/silver chloride (Ag/AgCl) reference electrode and a platinum (Pt) cathode for measurement of oxygen tension across the membrane. These devices do not rely on equilibration of the electrolyte. See Clark U.S. Pat. No. 2,913,386 issued Nov. 17, 1959. These devices use the semi-permeable membrane to limit the amount of oxygen reaching the cathode and therefore do not permit equilibration. This limited oxygen flow stabilizes the sensor, lowers its oxygen consumption and therefore causes minimal perturbation to the oxygen tension ambient in a sample.

The use of an Ag/AgCl reference electrode causes certain problems. Unfortunately, silver chloride dissolves in an aqueous solution and silver migrates to the cathode. The silver is plated on the cathode by the electric potential. This causes an increase in the size of the cathde resulting in an upward drift. This process is aggravated by high current, large Ag/AgCl areas, small electrode spacings, high temperature, small electrolyte volumes, and small cathode areas. Attempts to circumvent the plating problem have included the incidental solution set forth in Hunt et al. U.S. Pat. No. 4,512,349 which includes flushing an electrolyte solution through the electrodes. In the Hunt et al. device, use of an oxygen sensor as a subcutaneous tonometer is disclosed. The electrolyte actually equilibrates with the surrounding tissue fluid. Unfortunately, circulating electrolyte in a loop subcutaneously under the skin of a patient is not without difficulty. Further, while plating is inhibited by such techniques, it is not entirely prevented. Further, by equilibrating the electrolyte and operating the electrodes in a relatively rich oxygen content, plating is enhanced. This is especially true where small volumes of electrolyte are used.

Attempts to move away from Ag/AgCl electrodes have been made. Specifically, Clark U.S. Pat. No. 3,380,905 issued Apr. 30, 1968 entitled Electrolytic Sensor with Anodic Depolarization is such an attempt. In this reference it is disclosed to add a hydroquinone type additive to a two electrode oxygen sensor for measurement of oxygen tension across a semi-permeable membrane.

In Clark '905, oxygen tension is measured across a semi-permeable membrane. Extreme low current flow is produced having corresponding difficulty of measurement. Moreover, the sensor changes calibration with respect to the spacing of the membranes from the cathode. Where the semi-permeable membrane closes on the cathode, greater oxygen tension is measured, even though the oxygen tension on the membrane itself remains unchanged.

DISCOVER OF THE PROBLEM

It goes without saying that discovery of the problem can constitute invention. Accordingly, invention is claimed in research directed to a hydroquinone and the discovery of deficiencies in a quinhydrone electrode. trode.

We have discovered that quinhydrone electrodes have non-linearities in measuring oxygen tensions. This is true even where semi-permeable membranes are used to reduce oxygen tension and current flow in the measuring device. These non-linearities include excessive readings at low oxygen tensions and lower readings at high oxygen tensions. Further, such oxygen sensors take inordinate amounts of time to stabilize. Further, pressure sensitivity of these oxygen sensors prohibits their use subcutaneously where pressures cannot be controlled. Use in a clinical environment is severely limited: use in a tonometer environment could not be considered.

Semi-permeable membranes restrict the flow of gas (here oxygen) so that a tension differential exists across the membrane.

Where equilibration is utilized in place of an oxygen semi-permeable membrane, the use of a hydroquinone in an electrolyte is not taught by Clark. It is believed after the experimentation here referred to that current flow at the reference electrode of Clark perturbs the desired reference potential.

Further, the chemical reactions required in the two electrode Clark +905 patent produces the hydroxyl ion. This changes the pH of the electrolyte, further aggravating drift.

For these reasons, it is believed that the prior art has neglected hydroquinones as the depolarizing additives in equilibrating oxygen measurements. Quinhydrone electrodes are instead more commonly used for pH measurement.

This application will use the term equilibrating. This term will refer to the property of the disclosed tonometer where the oxygen tension exterior of the tonometer is substantially the same as the oxygen tension interior of the tonometer.

SUMMARY OF THE INVENTION

A closed tonometer for subcutaneous insertion is disclosed having a small closed equilibrating bath. Three noble metal electrodes, preferably platinum (Pt). communicate through electrical conductors to the bath at spacings exceeding 0.2 mm. Each noble metal electrode is typically exposed to the bath by embedding the noble metal in a dielectric and cutting both dielectric and electrode so that the exposed electrode is flush with and a part of the closed bath wall. The bath is contained within an oxygen permeable membrane—preferably Silastic ® a registered trademark of Dow Corning Corporation of Midland, Mich. The bath contains a sodium chloride (NaCl) solution, preferably 0.9%. and small amounts of a hydroquinone such as a tenth of a gram of pure ascorbic acid per 30 ml of NaCl solution. One of the noble metal electrodes becomes a quinhydrone reference electrode preserving a precise voltage differential with respect to the electrolyte bath. This voltage of the quinhydrone reference electrode is passed through a voltage follower amplifier to a voltage adder where it is added to a reference bias voltage. Output from the adder passes to a second electrode serving as an anode. The anode supplies current to the enclosed bath sufficient to maintain the bath at constant voltage with respect to the cathode. The current at the cathode is thus solely a function of oxygen tension equilibrated from the measured tissue. There results a tonometer of miniature dimension having true analytical output.

Other Objects, Features and Advantages of this Invention

An advantage of the disclosed invention is that the resultant closed tonometer is of small volume. Typical dimensions include a Silastic ® tube 52 thousandths outside diameter with one inch of length. It can be utilized subcutaneously with minimum patient inconvenience due to tonometer presence.

Another advantage of the disclosed electrode is fast initial stabilization. The electrode once placed rapidly settles to desired oxygen tension measurement.

An additional advantage of the tonometer is that it is pressure insensitive in that it relies on equilibration. Its calibration does not change with changes in pressure. Therefore. it is ideal for the subcutaneous environment where pressures may not be controlled.

A further advantage of the tonometer is that it contains a small closed bath which rapidly equilibrates with the oxygen tension of the surrounding tissue. Total bath contents can be 0.01 ml of fluid.

. Yet another advantage of the disclosed tonometer is that all of the electrodes are of noble metals. Plating and other destabilizing of the measuring cathode does not occur.

Yet another advantage of the disclosed tonometer is that its temperature dependency is reduced. Consequently, drifting of the readings responsive to patient fever is minimized.

A still further advantage of the invention is that the cell has high tolerance to outside interference. Consequently, rapid return to stabilized output occurs when the tonometer is perturbed by physical or electrical forces.

Yet a further advantage of the disclosed tonometer is that the electrodes can be located within extreme close proximity to one another. Separations of 0.5 mm center to center are preferred with separations of 0.2 mm being possible. Consequently, tonometer dimension is at a minimum.

An additional advantage of the noble metal electrodes is that all of the electrodes work with a very small spatial area contacting the bath. Accordingly, long lengths of electrodes extending into the bath are not required. Electrodes are not in danger of either breakage during assembly or breakage during use.

An additional advantage of the tonometer is that it is chemically neutral during measurement. There is no net oxygen consumption. Consequently, the small bath has long life. Tonometer emplacement need only occasionally occur.

A further feature of the lack of oxygen consumption is that it does not disturb the monitored site. Reduction of the diffusion requirements occurs, both to and from the tonometer as well as oxygen to and from the monitored site. Consequently, the oxygen profile of the site is rapidly followed.

A further object of this invention is to disclose a circuit for utilizing a three electrode tonometer. According to this, a hydroquinone reference electrode passes a voltage to a voltage following amplifier. The amplifier passes its output to a voltage adder and added to a reference bias voltage. The output of the adder is passed to an electrode acting as an anode. The anode passes sufficient current to the bath to maintain the bath at a constant and non-varying voltage with respect to the cathode. The cathode is thus able to have current flow solely as a function of oxygen tension: current flow does not otherwise vary.

An advantage of the disclosed circuitry is that the tonometer is analytical; that is to say a properly calibrated tonometer having a small enclosed bath provides laboratory standard measurements to attending physicians in a patient environment. Tonometer life can exceed more than one week.

BRIEF DESCRIPTION OF THE DRAWINGS

Other objects, features and advantages of the disclosed invention will become more apparent after referring to the following specification and attached drawings in which:

FIG. 1 is a side elevation section taken longitudinally at the tonometer:

FIG. 2 is a view taken along lines 2—2 of FIG. 1 illustrating the flush Pt electrodes:

FIG. 3 is an embodiment of the tonometer disposed within an encapsulated reference solution for shipping:

FIG. 4 illustrates the tonometer subcutaneously placed: and.

FIG. 5 illustrates schematically electrical circuitry for the operation of the tonometer.

The tonometer includes a molded plastic base fitting 14 having a three conductor shielded electrical cable 16 plugged therein. Connection fittings 18 providing electrical communication to each of the electrodes are provided.

The electrodes 22. 24. and 26 have Pt tips. Preferably the electrodes are spaced 0.5 mm apart. The electrodes are flush with the molded plastic base, preferably encased in glass and are wires 3 mils (0.003 of an inch) in diameter. Consequently. there is virtually no possibility of damage to the electrodes either during assembly or use.

Typically, electrodes 22, 24 and 26 are embedded in a dielectric, glass being preferred. Thereafter, the glass is polished away until the electrodes each form a part of the wall of the chamber containing the fluid bath.

Fitting 14 has a tube receiving sleeve 30. A Silastic ® tube 32 closed at an end 34 is threaded and force fitted over the sleeve. This tube is filled with solution S.

The actual tube dimensions are not only informative but form an important aspect of the utility of this invention. The Silastic ® tube is one and one-half inches long with one-half inch being threaded over fitting 14. The tube has an inner diameter of 0.35 thousandths. Total volume within the tube is 0.01 ml.

The solution S is distilled water with a 0.9% NaCl solution. A hydroquinone such as ascorbic acid is placed within the solution. We prefer placing a small amount 0.10 of a gram of pure ascorbic acid per 30 ml of solution. Iso-ascorbic acid and sodium ascorbate are also likely additives.

A table listing quinhydrone type additives follows:
QUINHYDRONE TYPE ADDITIVE
Benzoquinone
toluquinone
thymoquinone
1.4-napthoquinone
ascorbic acid (preferred)
iso-ascorbic acid (preferred)
sodium ascorbate (preferred)
iodide
potassium iodide
ferrocyanide thiocyanate
carbamylhydrazine
procaine
Adrenalin
hydroquinone
3.4-dihydroxy phenol
glutathione
cysteine
alpha-naphtylamine
sulfadiazine
phenothiazines
surfactants
detergents Reading the preceding list, the reader will understand that we require a non-toxic, preferably biocompatible neutral additive for the hydroquinone. Placement of the solution S within the Silastic ® tube 32 must be carefully done especially to restrict gaseous bubbles. Referring to patent application Ser. No. 787,224 filed Oct. 15, 1985 entitled Tonometer for Subcutaneous Oxygen Tension Measurement, a method satisfactory for the placement of the solution S within the tonometer is therein disclosed.

Regarding shipment of the tonometer, this can be best understood with respect to FIG. 3. Referring to FIG. 3, vial V having a cap C accommodates fitting 14 at flanges 40. The vial, like the interior of tube 32, contains a solution S. Preferably, the solution S has a reference molar solution of oxygen in a gas tight container in the interior of vial V. This way the tonometer can be calibrated and run until stabilized before actual placement in a patient.

Alternatively, the vial V can be supplied with a membrane for admitting an oxygen standard. For example, exposure of the membrane to atmosphere could provide vial V with a reference standard of oxygen. This allows multiple point calibration while mantaining sterility.

Placement of the tonometer for operation can be easily understood with respect to FIG. 4. Specifically, the skin S of a patient is shown in section having the tonometer T placed subcutaneously. The tonometer can be placed by any number of standard procedures including a Teflon ® catheter which can be removed once the tonometer is subcutaneously placed.

Electrodes 22. 24. and 26 are typically 0.5 mm spatial interval one from another. These electrodes can be spaced less than 0.5 mm without any interference in the electrical fields.

In the prior art, the tonometers operating life within a patient has been of concern. This concern is accentuated where the amount of solution within the Silastic ® tube is extremely small.

Here the life of a tonometer can exceed one week. That is to say that a single placement can stay within a patient for at least 96 hrs. for necessary measurements. Further. the Silastic ® tube has high physiological tolerance for most patients. Consequently, the tonometer usually only needs insertion once during an average duration of treatment.

Operation of the device can best be understood with respect to FIG. 5.

Referring to FIG. 5, quinhydrone electrode gives a very reproducible voltage with respect to the voltage of the electrolyte.

The voltage is output to an amplifier 50. Amplifier 50 provides a current flow across a divider including resistors 52 and 54 to a reference voltage source 56. The divider between resistors 52 and 54 outputs to an adder amplifier 57. Adder amplifier 57 maintains the voltage within solution S constant relative to the cathode 26 by placing sufficient current in the bath to cause the polarographic potential to be absolutely stable. By way of example. the voltage used with the pure ascorbic acid hydroquinone is ±0.6 of a volt.

Variation of current flow will only be caused by the variant of oxygen tension in the solution S. This current flow occurs across the polarographic potential. This range can vary: voltage from 0.4 volts to 0.8 volts can be used depending on cathode design. Accordingly. current outflow at cathode 26 passes to an amplifier 60 having a feedback resistance 62 there across. The amplifier 60 produces a voltage at output 64. The voltage at output 64 is directly proportional to the oxygen present.

The resulting half cell reactions for each electrode can be stated.

Taking a quinhydronone type additive Q:

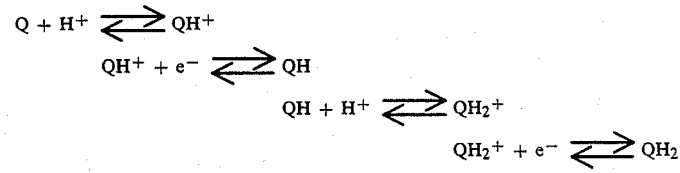

Therefore the reference reaction may be stated:

$$Q + 2H^+ + 2e^- \rightleftharpoons QH_2$$

Where Q is the quinhydrone type additive.
Th cathode reaction may be stated:

$$O_2 + 2H_2O + 4e^- \rightarrow 4OH^-$$

The anode reaction is reverse: it may be stated:

$$4OH^- \rightarrow O_2O + 4e^-$$

Thus, the anode-cathode hydroxyl and oxygen production cancels: the electrolyte remains unchanged over time.

The reader will understand that the tonometer incorporates some resistance between the respective electrodes. This is illustrated in the circuit schematic.

Likewise, the reader will realize that other circuits which in effect produce no current flow at the reference electrode 22 and maintain the solution S at a constant voltage with respect to the cathode in spite of changing current flow will suffice for the practice of this invention.

What is claimed is:

1. A tonometer for placement subcutaneously in a patient for the measurement of oxygen tension, said tonometer comprising:

an oxygen equilibrating tube, closed at one end and open at the other end;

a solution filling said tube, said solution including an electrolyte and a hydroquinone; a dielectric base plugging the open end of said tube to maintain said solution as a closed bath confined by said dielectric base and tube; and, said dielectric base having at least three nobie metal electrodes with attached conductors communicated to said closed bath, one of said electrodes comprising a reference electrode, said reference electrode measuring the voltage of aid solution filling said bath;

a second of said electrodes serving as an anode;

a third of said electrodes serving as a cathode;

means responsive to the voltage from said reference electrode to maintain the voltage at said anode such that the voltage between the bath and cathode remains constant and therefore the current between cathode and anode will be a function solely of oxygen tension in the equilibrated solution.

2. The invention of claim 1 and wherein said oxygen equilibraitn tube is Silastic ®.

3. The invention of claim 1 and wherein solution filling said tube includes a sodium chloride electrolyte.

4. The invention of claim 1 and wherein said hydroquinone is chosen from a group including ascorbic acid, iso-ascorbic acid and sodium ascorbate.

5. The invention of claim 1 and wherein said hydroquinone in said solution includes 0.10 of a gram per 30 ml of fluid.

6. The invention of claim 1 and wherein said three noble metal electrodes are flush with a wall of said dielectric base, said wall exposed to said closed bath.

7. The invention of claim 6 and wherein said noble metal electrodes are Pt.

8. A tonometer for placement subcutaneously of a patient having an attached circuit for the measurement of oxygen tension, said tonometer comprising:

an oxygen equilibrating tube, closed at one end and open at the other end;

a solution filling said tube, said solution including an electrolyte and a hydroquinone;

a dielectric base plugging said open end of said tube to maintain said solution as a closed bath confined by said dielectric base and tube, dielectric base having three noble metal electrodes with attached conductors communicated to said closed bath;

a circuit including a voltage follower amplifier having an input and an output, said input communicated to one of said electrodes acting as a reference electrode;

an adder amplifier having an input and an output, the input of said adder amplifier being communicated to the output of said voltage follower, the output of said adder amplifier outputting to a second one of said electrodes acting as an anode to maintain said solution at a polarographic voltage with respect to a third electrode acting as a cathode; and means for measuring current collected to said third electrode acting as a cathode whereby said cathode electrode acts as a current measurement electrode responsive to oxygen in said solution.

* * * * *